(12) United States Patent
Lastow et al.

(10) Patent No.: US 11,607,509 B2
(45) Date of Patent: Mar. 21, 2023

(54) DRY POWDER INHALER COMPRISING A CASING WITH A FIRST CASING PORTION AND A SECOND CASING PORTION

(71) Applicant: Iconovo AB, Lund (SE)

(72) Inventors: Orest Lastow, Torna Haellestad (SE); Lars Arvidsson, Dalby (SE)

(73) Assignee: Iconovo AB

( * ) Notice: Subject to any disclaimer, the term of this patent is extended or adjusted under 35 U.S.C. 154(b) by 307 days.

(21) Appl. No.: 16/648,649

(22) PCT Filed: Sep. 10, 2018

(86) PCT No.: PCT/SE2018/050905
§ 371 (c)(1),
(2) Date: Mar. 18, 2020

(87) PCT Pub. No.: WO2019/059826
PCT Pub. Date: Mar. 28, 2019

(65) Prior Publication Data
US 2020/0230332 A1 Jul. 23, 2020

(30) Foreign Application Priority Data
Sep. 19, 2017 (SE) .................................. 1751158-5

(51) Int. Cl.
*A61M 15/00* (2006.01)

(52) U.S. Cl.
CPC .... *A61M 15/0031* (2014.02); *A61M 15/0001* (2014.02); *A61M 15/0005* (2014.02);
(Continued)

(58) Field of Classification Search
CPC .......... A61M 15/0005; A61M 15/0026; A61M 15/0043; E05D 1/02
See application file for complete search history.

(56) References Cited

U.S. PATENT DOCUMENTS 3,596,822 A * 8/1971 Holley ................. B65D 43/162
D9/426
3,800,998 A * 4/1974 Gask ...................... B65D 75/52
206/362.4
(Continued)

FOREIGN PATENT DOCUMENTS

CN 1251536 A 4/2000
CN 1668354 A 9/2005
(Continued)

OTHER PUBLICATIONS

Chinese Search Report dated Jul. 14, 2022 for copending Chinese App. No. CN201880055407.0.
(Continued)

*Primary Examiner* — Kathryn E Ditmer
(74) *Attorney, Agent, or Firm* — Fishman Stewart PLLC

(57) ABSTRACT

A dry-powder inhaler may include a first casing portion, a second casing portion, and a hinge arrangement connecting the first casing portion and the second casing portion. The dry-powder inhaler may be assembled by folding the first casing portion and the second casing portion together. The first casing portion may include a cavity for receiving a dose blister foil, said cavity being adapted to contain a dry-powder medicament. The first casing portion and the second casing portion when folded together may be adapted to form an inlet for allowing a lidding foil extending out there from and an outlet for providing the medicament.

18 Claims, 3 Drawing Sheets

(52) U.S. Cl.
CPC .... *A61M 15/0028* (2013.01); *A61M 15/0043* (2014.02); *A61M 15/0051* (2014.02); *A61M 15/0026* (2014.02); *A61M 2202/064* (2013.01)

(56) References Cited

U.S. PATENT DOCUMENTS

| | | | | |
|---|---|---|---|---|
| 4,294,558 | A * | 10/1981 | Errichiello | G11B 33/0455 402/75 |
| 4,512,474 | A * | 4/1985 | Harding | B65D 75/225 220/4.23 |
| 4,703,853 | A * | 11/1987 | Byrns | G11B 23/0233 220/592.27 |
| 4,899,877 | A * | 2/1990 | Kiernan | B65D 75/245 206/349 |
| 6,102,035 | A | 8/2000 | Asking et al. | |
| 9,446,209 | B2 | 9/2016 | Richardson | |
| 2004/0065688 | A1 | 4/2004 | Duquet | |
| 2008/0190424 | A1 * | 8/2008 | Lucking | A61M 15/0043 128/203.15 |
| 2009/0084379 | A1 * | 4/2009 | Goeckner | A61M 15/0043 128/203.15 |
| 2009/0250058 | A1 * | 10/2009 | Lastow | A61M 15/0028 128/203.15 |
| 2012/0132204 | A1 | 5/2012 | Lucking et al. | |
| 2013/0233758 | A1 * | 9/2013 | Lu | B65D 75/225 206/587 |
| 2015/0343159 | A1 | 12/2015 | Farr | |
| 2016/0199596 | A1 * | 7/2016 | Stein | A61M 15/0091 128/203.15 |
| 2016/0346488 | A1 | 12/2016 | Beller | |
| 2016/0346490 | A1 * | 12/2016 | Beller | A61M 15/0021 |
| 2017/0000960 | A1 | 1/2017 | Richardson | |
| 2017/0119982 | A1 | 5/2017 | Jones | |
| 2017/0312458 | A1 * | 11/2017 | Beller | A61M 15/0008 |

FOREIGN PATENT DOCUMENTS

| | | | |
|---|---|---|---|
| CN | 104582772 A | 4/2015 | |
| CN | 106730186 A | 5/2017 | |
| DE | 102009041664 A1 * | 3/2011 | ........ A61M 15/0028 |
| EP | 1369140 A2 | 12/2003 | |
| GB | 2460281 A * | 11/2009 | .......... A61M 11/002 |
| JP | H11510412 A | 9/1999 | |
| JP | 2006280620 A | 10/2006 | |
| WO | 03095010 A2 | 11/2003 | |
| WO | WO-2015097034 A1 * | 7/2015 | ........ A61M 15/0028 |
| WO | WO-2015110832 | 7/2015 | |
| WO | WO-2016193379 | 12/2016 | |

OTHER PUBLICATIONS

Chinese Search Report dated Mar. 18, 2022 for copending Chinese App. No. CN201880055407.0 (w_English_transl.).

Japanese Office Action dated Mar. 29, 2022 for copending Japanese App. No. 2020512435 (with Eng. translation).

* cited by examiner

DRY POWDER INHALER COMPRISING A CASING WITH A FIRST CASING PORTION AND A SECOND CASING PORTION

CROSS-REFERENCE TO RELATED APPLICATIONS

This application claims priority to International Patent Application No. PCT/SE2018/050905, filed on Sep. 10, 2018, and Swedish Patent Application No. 1751158-5, filed on Sep. 19, 2017, the contents of both of which are hereby incorporated by reference in their entireties.

TECHNICAL FIELD

This invention pertains in general to the field of medicament inhalers, and more particularly to dry powder inhalers. The inhaler comprises a casing comprising a first casing portion, a second casing portion and a hinge arrangement connecting said first casing portion and second casing portion, whereby the inhaler is assembled by means of folding the first casing portion and the second casing portion together.

BACKGROUND

In the pharmaceutical field, with respect to treatment of respiratory and/or other diseases, inhalers have been widely used. Numerous drugs, medications and other substances are inhaled into the lungs for rapid absorption in the blood stream and for local action in the lung with such inhalers.

Inhaled drugs fall into two main categories, in form of liquids, including suspensions, and powders. The choice of category depends on the characteristics of the drugs, medications, etc., to be inhaled.

The most common type of inhaler is the pressurized metered-dose inhaler. In this type of inhaler medication is most commonly stored in solution in a pressurized canister that contains a propellant, although it may also be a suspension. The canister is attached to a plastic hand-operated actuator. On activation, the metered-dose inhaler releases a fixed dose of medication in aerosol form.

Another kind of inhaler is a nebulizer, which supply medication as an aerosol created from an aqueous formulation.

The kind referred to herein is yet another type, in form of a dry powder inhaler. A dry powder inhaler releases a pre-metered, capsuled dose or a device-metered dose of powdered medication that is inhaled through the inhaler. Inhalers with device-metered dose of powdered medication is normally inhalers with medication reservoir, containing powdered medication, from which metered doses are withdrawn through the use of different dose metering arrangements, said doses then being inhaled.

Unit dose dry powder inhalers are commonly used in order to ensure the hygiene as well as the proper dose of medicament being provided to the user. Unit dose dry powder inhalers contain an encapsulated dose and are disposed of after the dose has been inhaled.

Further, said inhalers does not require any dose-meter arrangements since they only contain one dose which makes them considerably less expensive to manufacture due to their less complex design.

Due to their low cost and one-dosage functionality, the unit dose dry powder are usually manufactured in large volumes, often by means of injection molding.

To guarantee the function of the inhaler, said inhaler requires the provision of several components inside its casing, such as blister foils, flow directing elements for a more optimal de-aggregation etc. Furthermore, the reservoir for containing the dose of medicament has to be filled with the appropriate dose.

Hence, the casing of the unit dose dry powder inhalers are traditionally manufactured in at least two separate casing parts, whereby the casing parts are provided with the necessary components and dosage.

Due to the large production volumes usually associated with the production of such one dose dry powder inhalers the consequent joining and handling of the multiple casing parts makes the manufacturing and assembly considerably more complex as well as more expensive.

In view of these drawbacks and limitations of the prior art, what is needed is a dry powder inhaler which can be assembled and manufactured in a less complex and more cost-efficient manner.

SUMMARY

Accordingly, the present invention preferably seeks to mitigate, alleviate or eliminate one or more of the above-identified deficiencies in the art and disadvantaged singly or in any combination and solves at least the above mentioned problems by providing a dry-powder inhaler comprising a casing, the casing comprising a first casing portion, a second casing portion and a hinge arrangement connecting said first casing portion and second casing portion; whereby the dry-powder inhaler is assembled by means of folding the first casing portion and the second casing portion together; whereby the first casing portion comprises a cavity for receiving the dose blister foil, said cavity being adapted to contain a dry-powder medicament; and whereby the first casing portion and second casing portion when folded together are adapted to form an inlet for allowing a lidding foil extending out there from and an outlet for providing the medicament.

Additionally, the present invention preferably seeks to mitigate, alleviate or eliminate one or more of the above-identified deficiencies in the art and disadvantages singly or in any combination and solves at least the above mentioned problems by providing a method for providing a dry-powder inhaler, whereby the method comprises providing a casing, the casing comprising a first casing portion, a second casing portion and a hinge arrangement connecting said first casing portion and second casing portion, the first casing portion and second casing portion being adapted to, when folded together, form an inlet for allowing a lidding foil extending out there from and an outlet for providing the medicament: and assembling the inhaler by means of folding the first casing portion and second casing portion together.

Further advantageous embodiments are disclosed in the appended and dependent patent claims.

BRIEF DESCRIPTION OF THE DRAWINGS

These and other aspects, features and advantages of which the invention is capable will be apparent and elucidated from the following description of embodiments of the present invention, reference being made to the accompanying drawings, in which.

DETAILED DESCRIPTION

The following description focuses on an embodiment of the present invention applicable to a medicament inhaler, and in particular a dry powder inhaler. However, it will be appreciated that the invention is not limited to this application but may applied to many other inhalers having an inlet and an outlet, as well as a medicament reservoir.

Figure 1:
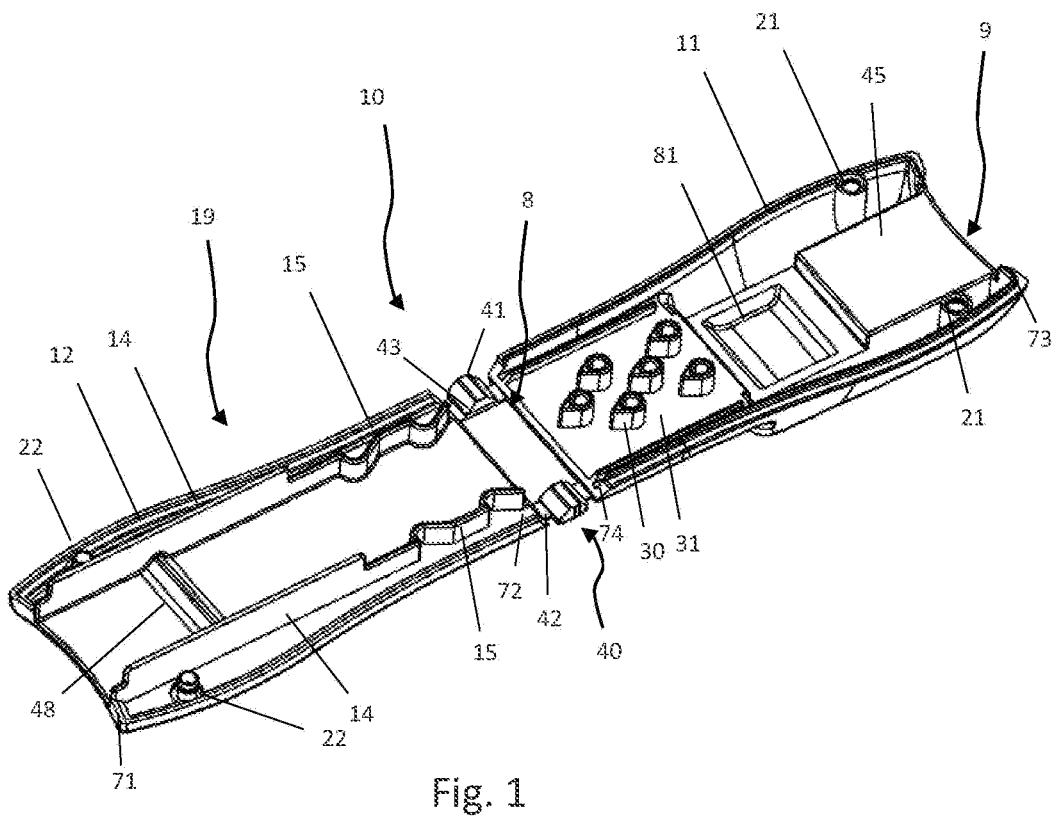
FIG. 1 is a perspective view of the inhalator of one embodiment without a lidding foil and the casing unfolded.

FIG. 1 shows a dry-powder inhaler 10. The dry-powder inhaler 10 comprises a casing 19, the casing preferably forming the outer shape of the dry-powder inhaler 10.

The casing 19 comprises a first casing portion 11 and a second casing portion 12, whereby the casing 19 further comprises a hinge arrangement 40 connecting the first casing portion 11 and the second casing portion 12.

Referring to said figure, the first casing portion 11 comprises a cavity 81 for receiving a lidding foil, the cavity 81 being adapted to contain the dry-powder medicament. This may for example be achieved by means of the lidding foil being heat sealed, such as welded, to the surrounding walls of the cavity 81 so as to seal away the cavity from the rest of the inside of the casing 19 and protect the medicament from moisture. Thereby, the dry-powder medicament may be kept in place during transport and handling of the inhaler 10 without any risk for leakage of dry-powder medicament through the inlet 9 and outlet 8 of the casing 19.

By means of the hinge arrangement 40 the inhaler 10 may be assembled by folding the first casing portion 11 and the second casing portion 12. The first casing 11 and the second casing portion 12 may thus when folded together be adapted to form an inlet 9 for allowing a lidding foil extending out there from and outlet 8 for providing the medicament.

As is conventional the user may thus operate the inhaler by means of first removing the lidding foil so as to expose the dry-powder medicament therein. The user may then inhale the medicament by means of inhaling at the outlet 8 thus allowing for the dry-powder medicament to flow through the casing of the inhaler 8 towards the user, whereby the inlet allow air to enter the casing and force the dry-powder medicament towards the inlet 8. The user may thus inhale the dry-powder medicament provided inside cavity 81 of the casing 19, whereby the treatment is finished and the inhaler 10 may be disposed of.

The casing which preferably may be in a plastic material such as PP or PE, may be manufactured by means of injection moulding. Due to the casing 19 being in one piece during at least the majority of the assembling due to the hinge arrangement 40 interconnecting the first casing portion 11 and the second casing portion 12 the transportation and assembly is made considerably less complex.

The hinge functionality allows for the for the casings to be transported and delivered in a simple manner since the casing portions may be connected prior to the insertion of the remaining components such as flow directing elements and lidding foils.

This is particularly advantageous due to the filling of the medicament and the sealing of said medicament inside the cavity 81 by. means of the lidding foil usually being performed at another location than the manufacturing of the casing 19. By connecting the casing portions prior to distribution to a site where filling and sealing medicament, the number of components to he handled during assembly and transport is reduced considerably, which allows for a more cost-efficient handling and transportation.

Further, the interconnected casing portions allows for a much more user-friendly and cost-efficient final assembly and filling of medicament since the filling and sealing operation does not require any complex and time consuming joining operations to be performed. Instead, the casing may just be folded together after being "loaded" with the dry-powder medicament.

The hinge functionality further allows for the entire casing 19 to be injection moulded in one piece whereby hinge arrangement 40 may be a foldable section of the casing 19 provided with a recess forming the outlet 8. Thereby, the entire casing may be manufactured in one production step which decreases the complexity and cost for assembling and manufacturing considerably compared to a conventional inhaler where the separate portions has to be handled separately and then mounted together.

The enablement of injection moulding of the entire casing in one piece further makes the casing far less susceptible for any tolerance errors since each cavity the casing is individual. Thereby, the first casing portion only needs to fit with the second casing portion moulded in the same cavity. In a conventional injection moulding process where the casing portions are injection moulded separately each first casing portion needs to fit with each second casing portion. This may lead to several casing portions having to be disposed of due to tolerance errors disallowing proper assembling. Hence, the enablement of injection moulding the entire casing in one piece allows for a more cost-efficient and reliable manufacturing process.

Further referring to FIG. 1, the inlet may be formed by the respective ends of the casing portions 11, 12 being provided with cut-outs, whereby said cut-outs are adapted to together form said inlet 9 when the casing is in the folded position. The hinge arrangement 40 is disposed between said first casing portion 11 and the second casing portion 12 so as to form a pivot axis.

Accordingly, the first casing portion 11 comprises a first end 73 and a second end 74, whereby the second casing portion 12 comprises a corresponding first end 71 and corresponding second end 72. The second ends 72, 74 are connected by means of the hinge arrangement 40 and may together with said hinge arrangement 40 form the outlet 8.

The inlet 9 may thus be formed by the first end 73 of the first casing portion 11 and the corresponding first end 71 of the second casing portion 12 when the casing is in the folded position. Each of the first end 73 and the corresponding first end 71 may comprise a cut-out extending along a plane orthogonal to a longitudinal axis of the inhaler 10, whereby the cut-outs together form the inlet 9 when the casing is in the folded position.

Again referring to FIG. 1, the first casing portion 11 further comprises a protruding shoulder 45 i.e. a shoulder which protrudes from the first casing portion 11 towards the second casing portion 12 when the casing 19 is in a folded position, whereby said protruding shoulder 45 is adapted to receive the lidding foil.

The protruding shoulder 45 is preferably disposed between the inlet 9 and the cavity 81 Preferably, said protruding should is disposed between the inlet 9 and the cavity 81 so as to together with the second casing portion 12 form the inlet 9 when the casing 19 is in a folded position.

This is particularly advantageous since the protruding shoulder may counteract the inherent hollow shape of the casing 19 around the inlet 9 in the folded position so as to achieve a more smooth transition between the casing portions around said inlet. Without the protruding shoulder there is a risk for the air flow becoming turbulent due to the casing forming a steep diverging portion just downstream of the inlet. This may cause some of the air flow to just pass by the cavity, whereby a larger air now is required in order to de-aggregate the dry-powder medicament inside the casing 19. The protruding shoulder 45 however reduces the diverging flow effect by directing the flow of air entering the inlet 9 and decreasing the diverging angle around the inlet 9, whereby a more efficient de-aggregation is achieved.

The inhaler 11 may further comprise at least one but preferably a plurality of flow directing elements 30 adapted to disaggregate the medicament Hence, the inhaler 10 comprises the flow directing elements 30 being disposed inside the casing between the cavity 81 and the outlet 8 of the inhaler. In other words, the flow directing elements may be disposed downstream of the cavity 81 and upstream of the outlet 8 when the casing is in a folded position.

The provision of the flow directing elements allows for directing of the air flow straight through the inhaler 10, i.e. from the inlet 9 to the outlet 8 for the medicament which achieves a more laminar flow pattern of air. This allows for more air to pass through the entire inhaler 10 with a single inhale, whereby a lower aggregation of medicament is achieved, hence increasing the potential of the medicament to reach out far in the lungs of the patient.

Additionally, the impinging effect on the air flow due to said flow directing element causes the powder contained in the air flowing through the inhaler during inhalation to collide with said flow directing elements and disperse even further, whereby an even lower aggregation may be achieved.

Said flow directing elements 30 may be integrated elements protruding from the first and/or second casing portion. The flow directing elements 30 may also be provided on a flow directing element insert, preferably in the shape of a plate to be received and attached to the first and/or second casing portion.

With advantage, the flow directing elements 30 may protrude from the first casing portion 11, i.e. the casing portion comprising the cavity 81. Due to the foldable design of the inhaler 10 a small gap is required between the flow directing elements and the casing portion which is not provided with said flow directing elements to ensure the ability to fold and interlocking of the two casing portions.

If the cavity 81 and the flow directing elements 30 are provided on the same casing portion, i.e. the first casing portion 11 the dry-powder medicament has to travel a substantial distance towards the second casing portion 12 from the cavity 81 in order to only pass through the gap and not pass through the flow directing elements 30. In the event of dry-powder medicament actually passing through said gap and traveling the sufficient distance towards the second casing portion 12 the kinetic energy of the particles of the dry-powder medicament has to be at such a high level that a sufficient low aggregation already is achieved. Comparatively, if the flow directing elements 30 are disposed on a casing portion different than the one being provided with the cavity 81, the particles of the dry-powder medicament would be allowed to enter through the gap far easier due to its closer distance to the cavity (i.e. the particles need to be provided with much lesser kinetic energy to pass through the gap).

Accordingly, the provision of the flow directing elements 30 on the first casing portion 30 decreases the risk for insufficient de-aggregation of the dry-powder medicament significantly.

To optimise and maximise the disaggregation of the medicament, the flow directing elements 30 are substantially drip shaped with their tapered end extending towards the outlet.

The second casing portion 12 comprises a set of inner walls 14 protruding from said second casing portion 12, the set of inner walls 14 extending parallel along the second casing portion 12, whereby each of the inner walls of the set of inner walls 14 has at least one inwardly directing portion 15 adapted to direct a flow inwardly towards the outlet 8. Thus the air flowing through the inhaler 10 may converge towards a longitudinal center axis of the inhaler, this reduces the risk for turbulence due to impinging effects in the vicinity of the outlet 8, i.e. due to the walls surrounding the outlet 8. More air is thus allowed to pass through the entire inhaler 10, i.e. from the inlet 9 to the outlet 8 during the inhalation which reduces the aggregation even further, allowing for more of the dry-powder medicament to enter the lungs of the user.

The inner walls 14 extend one on each side along a longitudinal centerline of the inhaler along the entire length of the casing 19 when the casing is in a folded position. Said inwardly directing portion 15 may be formed by the inner walls 14 having at least one tapered portion with a tapering angle directed diagonally inwardly towards the outlet 8 when the casing is in the folded position.

As the skilled person realizes said set of inner walls may also be provided on the first casing portion 11, whereby the first casing portion may comprise a set of inner walls 14 according to the above.

Said second casing portion 12 may further comprise a flow directing member 48 adapted to direct flow entering through the inlet 9 towards the cavity. Thus the air entering the inlet is forced towards the cavity of the first casing portion 11 whereby the cavity may be efficiently emptied of dry-powder medicament due to the dispersion effect of the air impinging on the bottom surface of the cavity 81. Thus an initial de-aggregation of the dry-powder medicament is achieved right away during inhalation which reduces the risk for dry-powder medicament getting stuck in the cavity as well as the risk for insufficient de-aggregation of medicament through the inhaler 10.

As shown in said FIG. 1, the flow directing member 48 may be a fin extending orthogonal to the longitudinal axis of the inhaler 10 i.e. along the width of the second casing portion 12, said fin may accordingly have an angular face adapted to impinge on the air moving through the inhaler 10 so as to direct it towards the cavity.

Preferably, said flow directing member 48 may extend between the inner walls 14 defining the longitudinal delimitations of the flow through area of the inhaler 10.

To retain the first casing portion 11 and the second casing portion 12 together in the folded position one of the casing portions 11, 12 may comprise at least one latching knob 22, whereby the other casing portion 11, 12 may comprise at least one aperture 21. The at least one aperture 21 is adapted to receive the at least one latching knob 22, so as to retain the casing portions 1 L 12 in a folded position. Thereby the casing portions may be latched together simply by the retaining properties of the material of the casing by means of the elastic deformation of the knob(s) and/or the material forming the aperture(s), whereby no additional mechanical fastening elements such as screws are required, resulting in a less complex and more cost-efficient assembling process.

Further referring to FIG. 1, the first casing portion 11. may be provided with a pair of apertures 21 for receiving a pair of knobs 22 provided on the second casing portion 12 when the casing is in a folded position. As depicted in said figure, the pair of knobs and the pair of apertures may be disposed on the respective casing portion so as to be on each side of the inlet 9 when the casing 19 is in the folded position.

Figure 2:
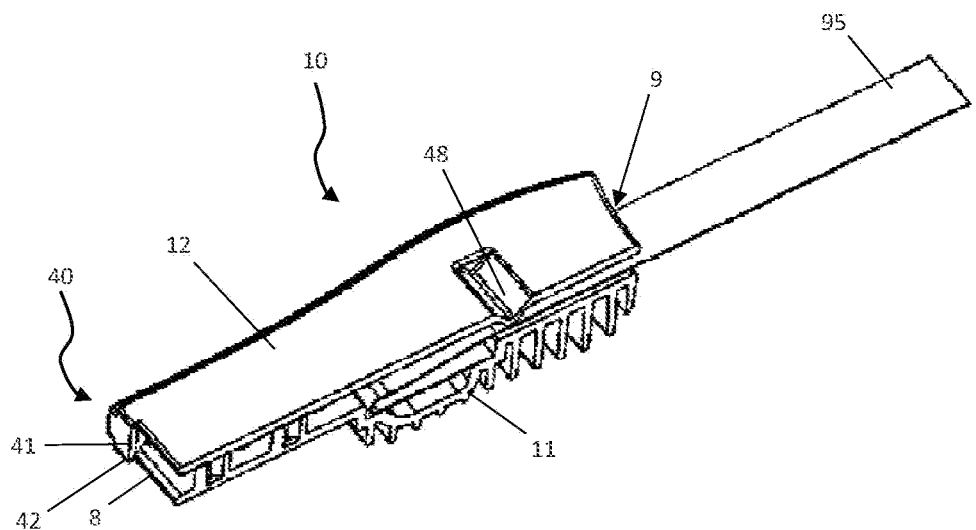
FIG. 2 is a longitudinal section view of the inhalator of one embodiment with a lidding foil and the casing folded.

Referring to FIG. 1 as well as FIG. 2, the hinge arrangement 40 comprises a folding portion 42 comprising support members 41 protruding therefrom, whereby the support members 42 are adapted to abut to the first casing portion 11 and the second casing portion 12 when said casing portions are folded together. The folding portion 42 accordingly defines the pivot axis of the casing 19, whereby the support members 41 are disposed parallel along the pivot axis defined by said by said folding portion 42. Thereby, the folding portion 42 by means of the support elements 41 together with the first and second casing portion form the outlet 8.

Said support members 41 guarantees a set distance between the first casing portion 11 and the second casing portion 12 around the outlet 8 when the casing 19 is in a folded position as a result of the abutting contact between the first casing portion 11 and the support members 42 and the second casing portion 12 and the support members 42.

Accordingly, the dimensions of the outlet 8 are not completely dependent on the dimensions of the first casing portion 11 and the second casing portion 12 forming the outlet 8. Instead the support members 42 define the set space forming the height of the outlet 8, whereby a homogenous, repeatable outlet which is less susceptible for fluctuating tolerances of the molded casing is achieved. If the outlet is solely defined by the walls of the casing any changes in the dimensions of said walls of the casing may affect the dimensions of the outlet 8, whereby the dose of medicament provided to the user and the inhalation power required to inhale the dose may vary from inhaler to inhaler. By providing the inhaler with said support members after the molding of the casing said problem will be mitigated in a cost-efficient manner.

Referring to FIG. 2, the folding portion 42 may comprise a pair of folding elements, each of which extending between and thereby interconnecting the first casing portion 11 and the second casing portion 12. The outlet 8 may thereby formed by the open space between the pair of folding elements which may be disposed substantially aligned with the lateral walls of the first casing portion 11 and the second casing portion 12.

Preferably, the support members 41 may be a pair of support members 41 which are formed by a pair protrusions one of each extending from the folding portion, i.e. from each of the pair of folding elements. Thereby, the hinge arrangement may be injection molded in one piece, whereby the entire casing and the entire hinge arrangement may be molded in one piece. This further reduces the cost of the manufacturing of the inhaler as well as reduces the risk for tolerance errors in the manufacturing process.

The support members 42 may each have a first phase of the adapted to abut to the first casing portion 11 when the casing 19 is in a folded position and a second phase adapted to abut to the second casing portion 12 when the casing 19 is in a folded position. The first and second phase of each support block 42 being parallel opposite surfaces.

Figure 3:
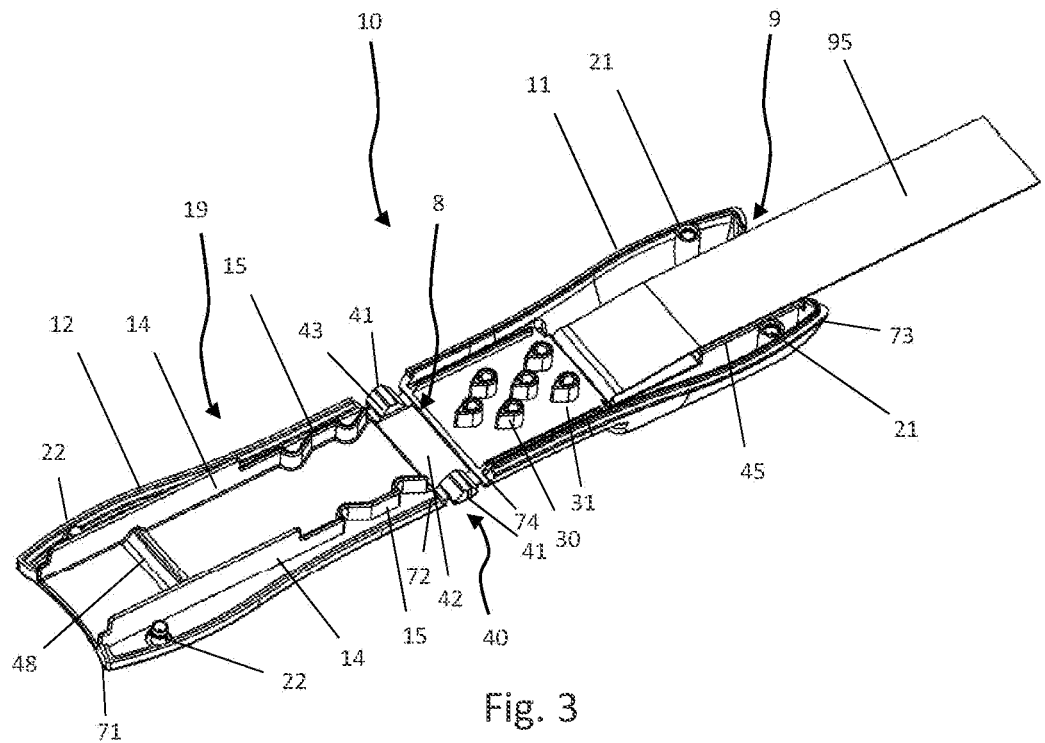
FIG. 3 is a perspective view of the inhalator of one embodiment with a lidding foil and the casing unfolded.

Referring to FIG. 3, to seal the medicament inside the medicament reservoir, the dry-powder inhaler 10 may comprise a lidding foil 95 being removably attached to the first casing portion 11 to seal the cavity adapted to contain a dry-powder medicament. The lidding foil may preferably be made of aluminium, due to its advantageous sealing properties.

With advantage the lidding foil 95 may be removably attached to the first casing portion 11 by means of heat sealing. However, mechanical fastening means such as a damp arrangement may be applicable as well.

Further, said lidding foil may also be removably attached to the protruding shoulder of the first casing portion 11, preferably by means of glue.

Figure 4:
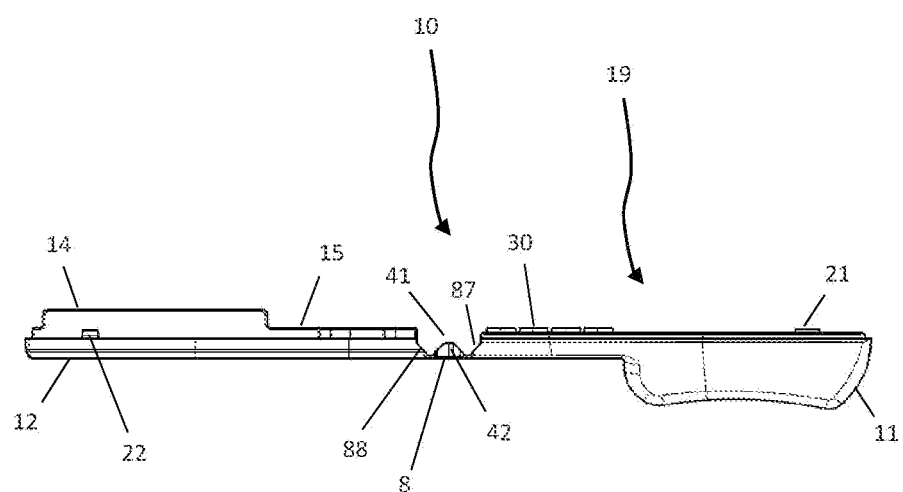
FIG. 4 is a side view of the inhalator of one embodiment without a lidding foil and the casing unfolded.

Turning to FIG. 4, the inhaler 10 is in a completely unfolded state with the lidding foil removed. Referring to said figure the support elements may have a substantially trapezoidal shape, whereby the bottom phases of the support elements are substantially wider than the top phases, i.e. the protruding phases of the support elements. The bottom phases preferably being aligned with the first casing portion 11 and the second casing portion 12 when the casing is in a fully unfolded state. The first casing portion 11 may accordingly comprise diagonal wall phases 87 adapted to abut to the diagonal phases of support elements 41. Correspondingly, the second casing portion 12 may comprise diagonal wall phases 88 adapted to abut to the corresponding diagonal phases of the support elements 41. Thus, a sufficient sealing is achieved in the joints between the casing portions and the support elements.

Figure 5:
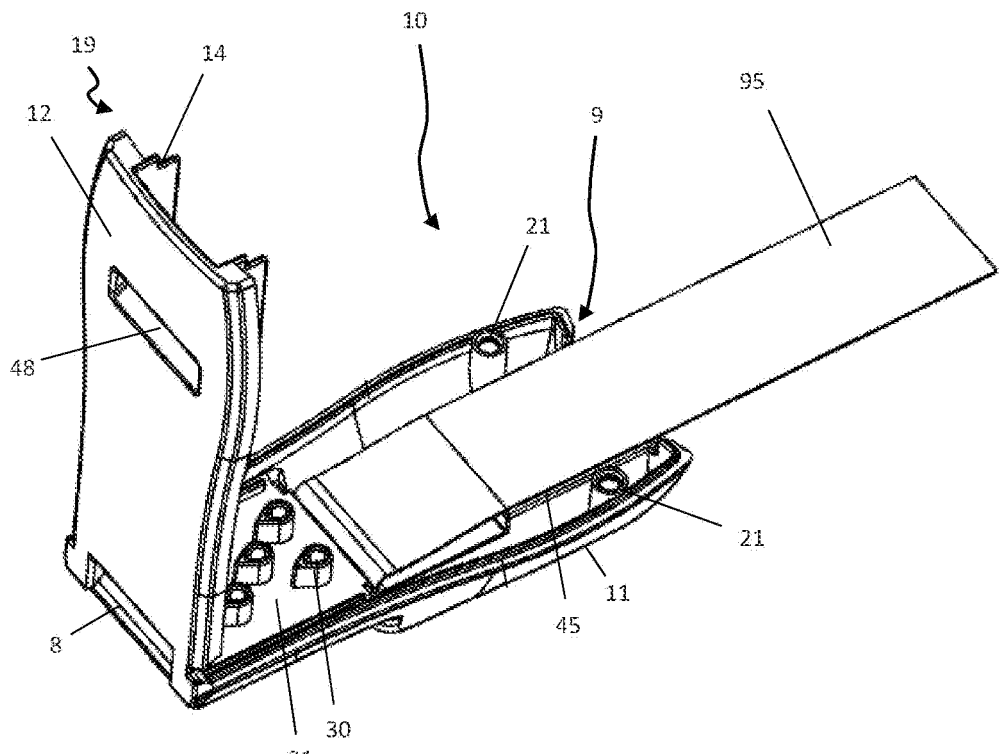
FIG. 5 is a perspective view of the inhalator of one embodiment with a lidding foil and the casing partially unfolded.

With reference to FIG. 5 which depicts the casing 19 of the inhaler 10 in a partially folded state, the first casing portion 11 may be positioned so as to be a bottom portion during the assembling of the inhaler 10.

This enables simple dosage of the dry-powder medicament which can be dosed into the cavity of the bottom casing portion, i.e. the first casing portion 11. Thereafter the blister foil 95 may be provided, whereby said blister foil 95 may be heat sealed to the cavity, i.e. the walls surrounding the cavity and the protruding shoulder 45.

At this stage the blister foil 95 is positioned so as to extend on top of said cavity and a significant distance outwardly from the first end of the first casing portion 11 partially forming the inlet 9.

Furthermore, the flow directing elements 30 may be attached to the first casing portion 11. Preferably this is performed by means of the flow directing elements 30 being provided on a now directing element insert 31 adapted to be fastened to the first casing portion 11. Said flow directing element insert 31 being a plate for fastening to the first casing portion 11, whereby the flow directing elements 30 protrude towards the second casing portion 12 from the insert 31 when the casing is in the folded position.

Finally, the casing portions may be folded together, whereby the casing portions are brought into contact with each other thus forming the casing of the inhaler 10.

Figure 6:
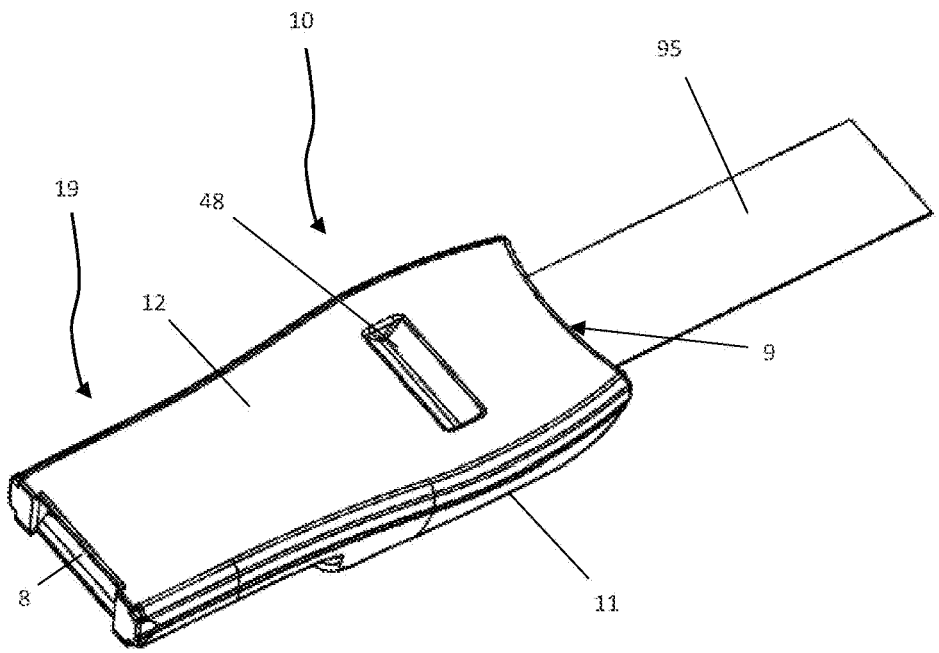
FIG. 6 is a perspective view of the inhalator of one embodiment with a lidding foil and the casing folded.

Referring to FIG. 6, the casing portion in a fully folded state is shown. As seen in said figure, the outlet 8 may be formed by the second casing portion 12 comprising a recess for providing the medicament.

Further referring to FIG. 6, the flow directing member 48 may be formed by a an inward protrusion in the form of a dimple extending into the inner of the casing, i.e. towards the first casing portion 12 when the casing is in the folded position.

Present invention. may further relate to a method for providing a dry-powder inhaler, whereby the method comprises providing a casing 19, the casing 19 comprising a first casing portion 11, a second casing portion 12 and a hinge arrangement 40 connecting said first casing portion 11 and second casing portion 12, the first casing portion 11 and second casing portion 12 being adapted to, when folded together, form an inlet 9 for allowing a lidding foil 95 extending out there from and an outlet 8 for providing the medicament; the method further comprising assembling the inhaler 10 by means of folding the first casing portion 11 and second casing portion 12 together.

The method may also comprise connecting the first casing portion 11 and the second casing portion by means of the hinge arrangement 40 so as to form the casing 19, prior to the folding of said casing 19.

Alternatively, the method may comprise injection molding the casing 19 prior to the folding of said casing 19, whereby the first casing portion 11, the second casing portion 12 and the hinge arrangement 40 are integrated parts of said casing portion 18.

Although, the present invention has been described above 'with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dry-powder inhaler comprising a casing having:
    a first casing portion including a first end and a second end;
    a second casing portion including a corresponding first end and a corresponding second end;
    a hinge arrangement connecting the first casing portion and the second casing portion, the hinge arrangement comprising an outlet;
    wherein the second end of the first casing portion and the corresponding second end of the second casing portion are connected via the hinge arrangement;
    wherein the dry-powder inhaler is assembled by folding the first casing portion and the second casing portion together via the hinge arrangement;
    wherein the first casing portion includes a cavity for receiving a lidding foil, said cavity being adapted to contain a dry-powder medicament;
    wherein the first casing portion and the second casing portion when folded together are adapted to form (i) an inlet proximate the first ends for allowing the lidding foil to extend out therefrom and (ii) the outlet proximate the second ends for providing the medicament to a user; and
    wherein the second casing portion comprises a flow directing member, the flow directing member being disposed between the cavity and the inlet when the first casing portion and the second casing portion are folded together, the flow directing member adapted to direct flow entering through the inlet towards the cavity.

2. The inhaler according to claim 1, comprising the lidding foil removably attached to the first casing portion so as to seal the cavity.

3. The inhaler according to claim 2, wherein the lidding foil is removably attached to the first casing portion via glue.

4. The inhaler according to claim 2, wherein the lidding foil is made of aluminum.

5. The inhaler according to claim 1, wherein the first casing portion includes a protruding shoulder adapted to receive the lidding foil.

6. The inhaler according to claim 1, further comprising flow directing elements adapted to disaggregate the medicament, said flow directing elements being disposed inside the casing between the cavity and the outlet when the first casing portion and the second casing portion are folded together.

7. The inhaler according to claim 6, wherein the flow directing elements protrude from the first casing portion.

8. The inhaler according to claim 6, wherein the flow directing elements are each tear shaped with a tapered end extending towards the outlet.

9. The inhaler according to claim 1, wherein the second casing portion comprises a set of inner walls protruding from said second casing portion, the set of inner walls extending along the second casing portion, wherein each of the inner walls of the set of inner walls has at least one inwardly directing portion adapted to direct a flow inwardly towards the outlet.

10. The inhaler according to claim 1, wherein one of the casing portions comprises at least one latching knob and the other casing portion comprises at least one aperture adapted to receive the at least one latching knob so as to retain the casing portions in a folded position.

11. The inhaler according to claim 1, wherein the hinge arrangement comprises a folding portion comprising support members protruding therefrom, wherein the support members are adapted to abut to the first casing portion and the second casing portion when said casing portions are folded together.

12. A method for providing a dry-powder inhaler, the method comprising:
    providing a casing having (i) a first casing portion including a first end and a second end, (ii) a second casing portion including a corresponding first end and a corresponding second end, and (iii) a hinge arrangement connecting said first casing portion and said second casing portion, the hinge arrangement comprising an outlet, wherein the second end of the first casing portion and the corresponding second end of the second casing portion are connected via the hinge arrangement, wherein the first casing portion includes a cavity for receiving a lidding foil, said cavity being adapted to contain a dry-powder medicament, the first casing portion and the second casing portion being adapted to, when folded together, form an inlet for allowing the lidding foil to extend out therefrom and the outlet for providing a medicament to a user, wherein the second casing portion comprises a flow directing member, the flow directing member being disposed between the cavity and the inlet when the first casing portion and the second casing portion are folded together, the flow directing member adapted to direct flow entering through the inlet towards the cavity; and
    assembling the inhaler by folding the first casing portion and second casing portion together via the hinge arrangement.

13. The method according to claim 12, further comprising removably attaching the lidding foil to the first casing portion so as to seal the cavity of the first casing portion.

14. The method according to claim 13, wherein the lidding foil is attached to a protruding shoulder of the first casing portion.

15. The method according to claim 12, wherein the casing includes flow directing elements disposed between the cavity of the first casing portion and the outlet and adapted to disaggregate the medicament.

16. The method according to claim 15, wherein the flow directing elements protrude from the first casing portion.

17. The method according to claim 15, wherein the flow directing elements are each tear shaped with a tapered end extending towards the outlet.

18. The method according to claim 12, wherein the second casing portion comprises a set of inner walls protruding from said second casing portion, the set of inner walls extending along the second casing portion, wherein each of the inner walls of the set of inner walls has at least one inwardly directing portion adapted to direct a flow inwardly towards the outlet.

\* \* \* \* \*